(12) United States Patent
Scheffel et al.

(10) Patent No.: US 7,976,689 B2
(45) Date of Patent: Jul. 12, 2011

(54) GAS SENSOR

(75) Inventors: Marcus Scheffel, Gerlingen (DE);
Holger Reinshagen, Bamberg (DE);
Lothar Diehl, Gerlingen (DE); Thomas Seiler, Stuttgart (DE)

(73) Assignee: Robert Bosch GmbH, Stuttgart (DE)

( * ) Notice: Subject to any disclaimer, the term of this patent is extended or adjusted under 35 U.S.C. 154(b) by 210 days.

(21) Appl. No.: 12/294,346

(22) PCT Filed: Feb. 26, 2007

(86) PCT No.: PCT/EP2007/051804
§ 371 (c)(1),
(2), (4) Date: Dec. 8, 2008

(87) PCT Pub. No.: WO2007/110291
PCT Pub. Date: Oct. 4, 2007

(65) Prior Publication Data
US 2009/0107839 A1   Apr. 30, 2009

(30) Foreign Application Priority Data

Mar. 28, 2006 (DE) .......................... 10 2006 014 681

(51) Int. Cl.
*G01N 27/41* (2006.01)
(52) U.S. Cl. .................. 204/406; 204/425; 72/23.32
(58) Field of Classification Search .................. 204/406, 204/425, 427; 205/784.5, 785; 73/23.31, 73/23.32
See application file for complete search history.

(56) References Cited

U.S. PATENT DOCUMENTS

| 4,787,966 | A |   | 11/1988 | Nakajima et al. | |
| 5,895,564 | A | * | 4/1999 | Miyata et al. | 205/784.5 |
| 5,929,328 | A | * | 7/1999 | Seidenfuss | 73/114.73 |
| 5,976,335 | A | * | 11/1999 | Kato et al. | 204/425 |

FOREIGN PATENT DOCUMENTS

| DE | 39 05 298 | 9/1989 |
| DE | 39 17 710 | 1/1990 |
| DE | 102 57 284 | 6/2004 |
| EP | 0 125 069 | 11/1984 |
| EP | 0 281 378 | 9/1988 |
| EP | 0 849 590 | 6/1998 |
| WO | WO 01/27602 | 4/2001 |

* cited by examiner

*Primary Examiner* — Kaj K Olsen
(74) *Attorney, Agent, or Firm* — Merchant Gould P.C.

(57) ABSTRACT

The invention relates to a gas sensor for determining the oxygen concentration in a gas mixture, especially in the exhaust gas of internal combustion engines. Said gas sensor comprises a pump cell having an outer pump electrode, exposed to the gas mixture, and an inner pump electrode, exposed to the gas mixture via a diffusion barrier, and a solid electrolyte body interposed between the outer pump electrode and the inner pump electrode. The gas sensor also has a reference electrode, exposed to a reference gas, and a sensor heating device. The outer pump electrode is connected to a circuit arrangement via a pump current line, the inner pump electrode via a measuring line, the reference electrode via a reference current line and the sensor heating device via two heating lines. The invention is characterized in that the pump current line and one heating line are electrically interconnected and grounded, the pump current can be supplied via the measuring line and the Nernst voltage can be tapped between the measuring line and the reference pump current line and the reference pump current flows from the reference electrode to the outer pump electrode.

5 Claims, 2 Drawing Sheets

GAS SENSOR

TECHNICAL FIELD

The invention proceeds from a gas sensor according to the class of the claims.

BACKGROUND

Such a gas sensor proceeds, for example, from the German patent DE 102 57 284 A1. In the case of this gas sensor, wherein the sensor heating device is operated in a clocked circuit in order to introduce the heat output required at any one time into the sensor element, the sensor heater is provided with two supply lines. Moreover, provision is made for a pump current line, a measuring line as well as a reference pump current line for the pump cell and the Nernst cell. A common ground line is used for the pump cell and the Nernst cell.

Connectors, which must contain six terminals, are required for establishing contact for such a broadband probe. Additional lines and connecting pins require an additional manufacturing complexity and cause additional costs. Moreover, a use of standard connectors is not implicitly possible. It is also a disadvantage that a drop in voltage between the ground of the internal combustion engine and the ground of the circuit arrangement, which, for example, is constituted by a control unit, is variable depending on current load; and if the connection is corroded, said drop in voltage can exceed approximately 1V and thereby the Nernst voltage.

Moreover, a disturbance in the output signal, which is not desirable, can arise in the sensor element by way of the coupling of the clocked heating device with the Nernst cell. A coupling of the heating current into the signal line can cause considerable disturbances in the operation of the gas sensor.

SUMMARY

The gas sensor according to the invention with the characteristics of the claims has in contrast the advantage that a signal line and therefore also a connecting pin can be omitted because the pump current line and a heating line are electrically interconnected and grounded. Thus, the pump current can be advantageously supplied via the measuring line and the Nernst voltage can be advantageously tapped between the measuring line and reference pump current line. On the basis of this circuit, the drop in voltage at the clocked heating line in fact changes the necessary pump voltage; however, the measured pump current continues to flow only through the pump cell. Furthermore, it is advantageous that the Nernst voltage does not have an offset.

Advantageous modifications and improvements of the gas sensor indicated in the independent claim are possible by way of the measures listed in the dependent claims.

Provision is made in a preferred form of embodiment for the heating device to be impressed with a high-side FET clocked voltage. Otherwise the ground of the closed-loop control electronics would have to lie at battery voltage $U_{Batt}$.

When a ground offset is present, the Nernst voltage is advantageously acquired by an instrumentation amplifier arranged between the measuring line and the reference pump current line.

Provision is made in an advantageous form of embodiment for a temperature measurement of the sensor element by measuring the internal resistance of the Nernst cell and/or the resistance of the sensor heating device.

BRIEF DESCRIPTION OF THE DRAWINGS

Examples of embodiment of the invention are depicted in the drawings and are described in detail in the following description.

The following are shown.

DETAILED DESCRIPTION

Figure 1:
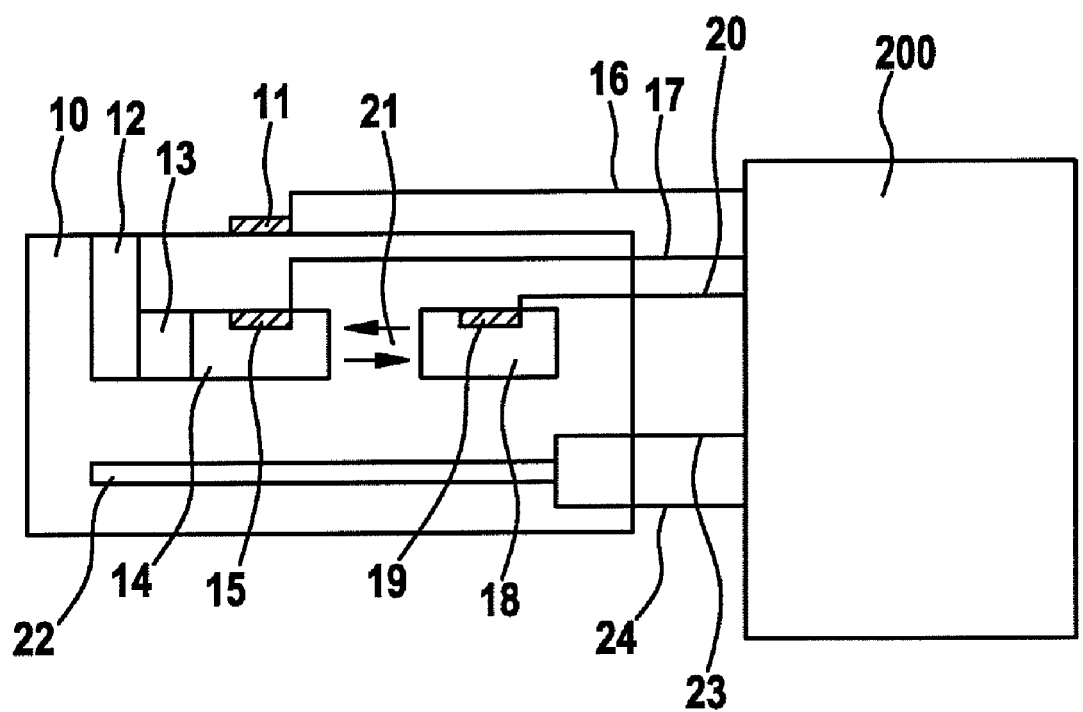
FIG. 1 schematically depicts a sensor element of a gas sensor, which is known from the technical field.

The gas sensor 10 shown in FIG. 1 contains a first electrode, also referred to as the outer pump electrode 11, which is exposed to a gas to be analyzed. The gas, which is to be analyzed, passes via a gas flue 12 and a diffusion barrier 13 into a gas measuring chamber 14, wherein a second electrode, also referred to as the inner pump electrode 15, is disposed. A pump cell originates between the first and the second electrode 11, 15. The first electrode 11 is connected to a pump current line 16 and the second electrode 15 to a measuring line 17.

The gas sensor 10 contains a reference gas chamber 18, wherein a third electrode 19 is disposed, which is connected to a circuit arrangement via a reference pump current line 20. A Nernst cell, wherein a reference gas ion transport 21 can take place, originates between the reference gas chamber 18 and the gas measuring chamber 14 in the same manner as between the electrodes 11, 15.

Figure 2:
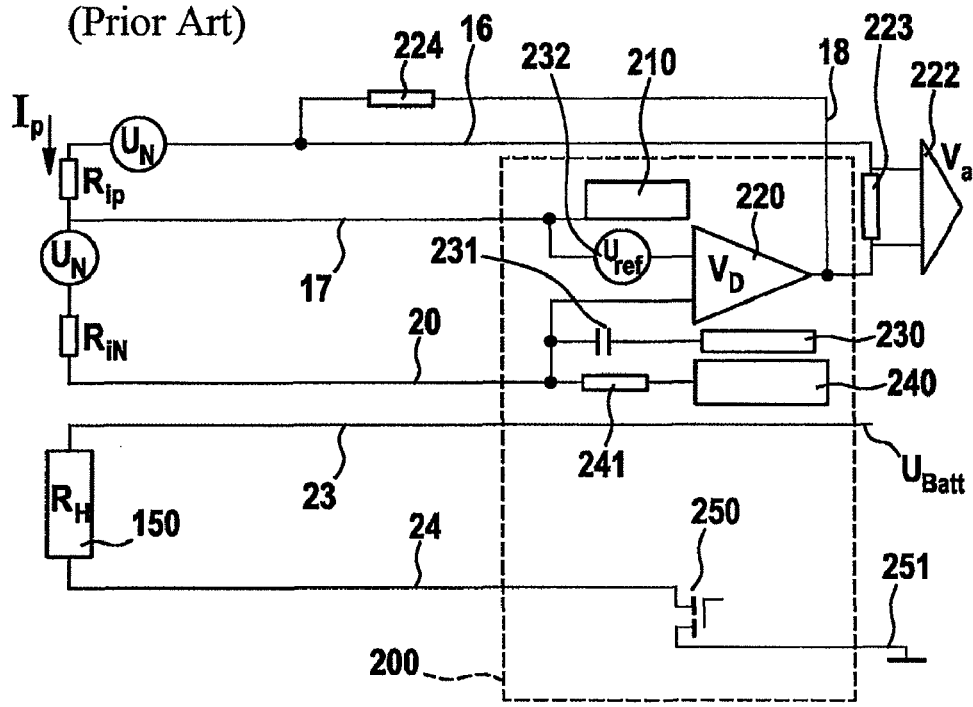
FIG. 2 is a circuit diagram of a gas sensor known from the technical field.

The gas sensor 10 furthermore contains a sensor heating device 22, which is provided with two heating lines 23, 24. The pump current line 16, the measuring line 17, the reference pump current line 20 and the heating lines 23, 24 are supplied to a control unit, as it is schematically depicted in FIG. 2. For this purpose, provision is made, for example, for connectors, which have connecting pins, whose number corresponds to the number of lines.

An equivalent circuit diagram of such a gas sensor as well as a detailed configuration of the circuit arrangement 200, which is, for example, part of a control unit, is schematically depicted in FIG. 2.

By means of the reference pump current line 20, a reference pump current, which is provided by a current source 240, is supplied to the third electrode 19 via a resistor 241. The reference pump current source 240 is furthermore connected to the inverting inlet of a differential amplifier 220, whose outlet provides a pump current $I_p$ via a working resistor 223. The pump current $I_p$ is identical to a sensor signal, which is amplified in an amplifier 222. The pump current $I_p$ is supplied to the outer pump electrode 11 via the pump current line 16. A voltage, which is tapped by means of the measuring line 17 and is supplied to the non-inverting inlet of the differential amplifier 220, drops across a resistance $R_{ip}$ developed by the sensor element between the outer electrode 11 and the inner electrode 12. The measuring line 17 is connected to a virtual ground 210 and to a reference voltage source 232. The reference voltage source 232 is connected to the non-inverting inlet of the differential amplifier 220.

The heating device, which is provided with a heating resistor 150, is connected via the two lines 23, 24 to the battery voltage $U_{Batt}$ as well as to the low-side FET 250, which itself has a connection to the common ground 251 of the circuit arrangement 200. A portion of the pump current $I_p$ is transported via a balancing line 18 and a balancing resistor 224, which is parallel to the measuring resistor 223 and which can be adjusted to calibrate the probe signal. This circuit of the broadband sensor requires in this instance six lines.

Figure 3:
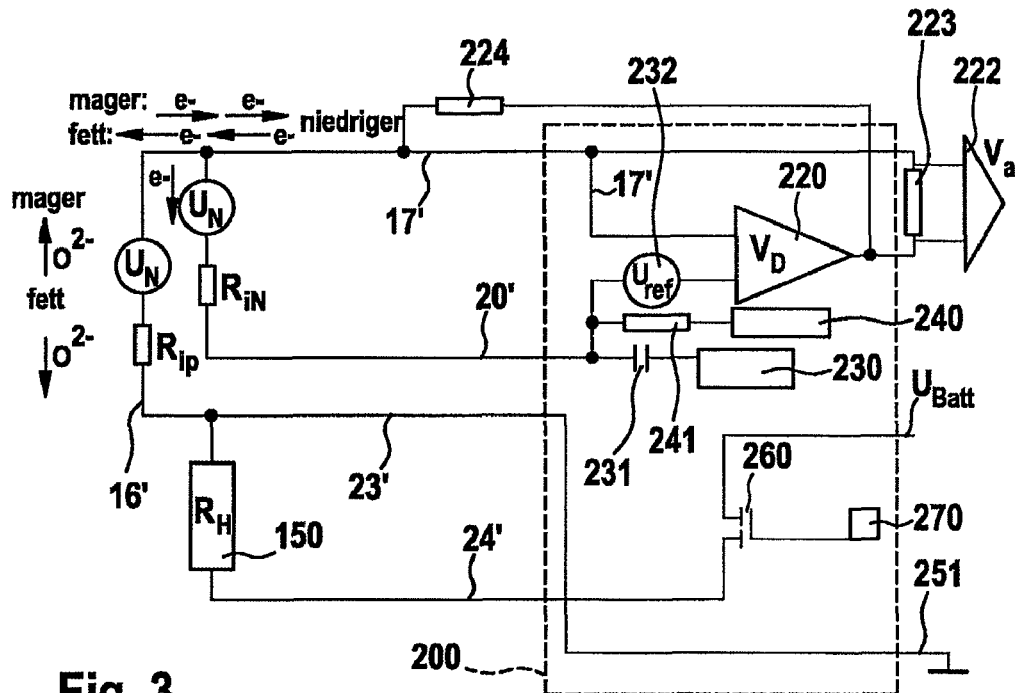
FIG. 3 is a circuit diagram of a gas sensor according to the invention.

In order to reduce the number of lines, provision is made in the gas sensor according to the invention, which is depicted in FIG. 3, for the outer pump electrode to be electroconductively connected to the heating line 23'. This heating line 23' leads in turn to the common ground 251 of the circuit arrangement, for example the control unit ground of a control unit 200. The second heating line 24' is connected to the heating resistor 150 of the sensor heating device via a high-side FET, which is clock activated by a clocking device 270. In the case of this gas sensor, the pump current is supplied via the measuring line 17' and also measured there. The measuring line 17' is fed to the non-inverting inlet of the differential amplifier 220 in order to measure the Nernst voltage between the inner pump electrode 15 and the third electrode 19. The reference pump current, which is provided by the current source 240, is supplied via the reference pump current line 20' in an inherently known manner. For this purpose, the pump current transformer is designed as a bipolar configuration because a negative pump current must be supplied to the pump cell.

The Nernst voltage is tapped via an instrumentation amplifier between the second electrode, i.e. the inner pump electrode 15, and the third electrode 19. In this case, the reference voltage source 232 is connected to the inverting inlet of the differential amplifier 220.

In the case of the gas sensor known from the technical field, which is depicted in FIG. 2, as well as in the case of the gas sensor according to the invention, which is depicted in FIG. 3, a measurement of the internal resistance of the gas sensor is carried out via a capacitance 231 by a switching mechanism. On the basis of the measurement of the internal resistance of the Nernst cell, the temperature of the gas sensor can be suggested. A temperature can also alternatively be determined by measuring the heating resistance. The current for the pumped reference is supplied via the reference pump current line 20' of the third electrode 19 and flows across the outer pump electrode 11. For this reason, the oxygen in the outer pump electrode is pumped out, and an offset of the pump current signal does not occur as a result of the oxygen being pumped out of the inner pump electrode 15. The reference pump current signal therefore does not have an offset.

The gas sensor at hand described in connection with FIG. 3 has the distinct advantage vis-à-vis one known from the technical field in that only five instead of six lines are required here. The voltage drop of the clocked heating line does in fact change the necessary pump voltage; however, the measured pump current continues to flow only through the pump cell.

The invention claimed is:

1. A gas sensor for determining an oxygen concentration in an exhaust gas of an internal combustion engine with a pump cell, comprising:
    an outer pump electrode exposed to the exhaust gas, wherein the outer pump electrode is connected to a circuit arrangement via a pump current line;
    an inner pump electrode exposed to the exhaust gas via a diffusion barrier, wherein the inner pump electrode is connected to the circuit arrangement via a measuring line;
    a solid electrolyte body interposed between the outer pump electrode and the inner pump electrode;
    a reference electrode exposed to a reference gas, wherein the reference electrode is connected to the circuit arrangement via a reference pump current line;
    a sensor heating device, wherein the sensor heating device is connected to the circuit arrangement via a plurality of heating lines; and
    an instrumentation amplifier adapted to acquire a Nernst voltage between the measuring line and the reference pump current line;
    wherein the pump current line and one of the plurality of heating lines are electrically coupled, including a grounded node, and wherein the measuring line is adapted to supply a pump current, and wherein the reference pump current line is adapted to supply a reference pump current to the reference electrode and from there to the outer pump electrode.

2. A gas sensor according to claim 1, further comprising a high-side FET adapted to clock a voltage applied to the sensor heating device.

3. A gas sensor according to claim 1, further comprising a gas measuring chamber in which the inner pump electrode is disposed.

4. A gas sensor according to claim 1, further comprising a reference gas chamber in which the reference electrode is disposed.

5. A gas sensor according to claim 1, further comprising a switching mechanism adapted to measure an internal resistance of the gas sensor, based upon which a temperature of the gas sensor is determined.

* * * * *